United States Patent [19]

Baldwin

[11] 4,060,601

[45] Nov. 29, 1977

[54] CERTAIN LOWER-ALKYL AMINO-2'-HYDROXY-PROPOXY PYRIDINES

[75] Inventor: John J. Baldwin, Lansale, Pa.

[73] Assignee: Merck & Co., Inc., Rahway, N.J.

[21] Appl. No.: 696,237

[22] Filed: June 15, 1976

[51] Int. Cl.² .................. C07D 213/50; C07D 213/52; A61K 31/395
[52] U.S. Cl. .............................. 424/263; 260/294.8 F; 260/296 AE; 260/295 R; 260/296 R
[58] Field of Search ................. 260/294.8 F, 296 AE; 424/263

[56] References Cited

U.S. PATENT DOCUMENTS

| | | | |
|---|---|---|---|
| 3,946,009 | 3/1976 | Wasson et al. | ................ 260/247.5 D |
| 4,000,282 | 12/1976 | Baldwin | ............................ 260/294.9 |

*Primary Examiner*—Alan L. Rotman
*Attorney, Agent, or Firm*—Daniel T. Szura; Rudolph J. Anderson, Jr.

[57] ABSTRACT

Novel substituted (3-loweralkylamino-2-$R_1$O-propoxy)-pyridines, their pharmaceutically acceptable salts and their preparation are disclosed. These pyridines have pharmaceutical properties such as anti-hypertensive activity of rapid onset.

26 Claims, No Drawings

CERTAIN LOWER-ALKYL AMINO-2'-HYDROXY-PROPOXY PYRIDINES

BACKGROUND OF THE INVENTION

The present invention concerns substituted (3-loweralkylamino-2-$R_1$O-propoxy)pyridines having pharmaceutically useful properties.

Hypertension in man and other animals can be treated with various chemical agents. One such class of agents is that known as the β-adrenergicc blocking agents or β-blockers. While this class of agents can have antihypertensive activity, the onset of this activity is generally gradual. The structure and activity of β-blockers is generally discussed in "Clinical Pharmacology and Therapeutics" 10, 252, 306 (1969). Substituted carbocyclic aryl β-adrenergic blocking agents are disclosed in British Pat. No. 1,206,420, British Pat. No. 1,304,303 U.S. Pat. No. 3,644,636, U.S. Pat. No. 3,459,782, Belgian Pat. No. 707,050 and Netherlands Pat. No. 69.07700. Substituted N-heteroaryl β-adrenergic blocking agents are also disclosed in German application No. 2,406,930, its counterpart South African Pat. No. 74 28204, British Pat. No. 1,305,644, Journal of Medicinal Chemistry 16, 1113–1114 (1973) and Journal of Medicinal Chemistry 15, 1321 (1972).

Another class of anti-hypertensive agents are the vasodilators. Vasodilators, however, normally cause undesirable tachychardia.

Novel substituted (3-loweralkylamino-2-$R_1$O-propoxy)pyridines have been discovered. These compounds have antihypertensive activity of rapid onset. Many of the compounds also have vasodilator activity and are β-adrenergic blocking agents.

SUMMARY OF THE INVENTION

Novel substituted (3-loweralkylamino-2-$R_1$O-propoxy)pyridines and their pharmaceutically acceptable salts which have rapid anti-hypertensive effect.

DESCRIPTION OF THE PREFERRED EMBODIMENTS

An embodiment of the present invention is compounds having the formula

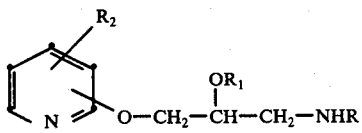

I wherein
R is $C_3$–$C_4$ branched alkyl,
$R_1$ is H or

wherein L is selected from $C_1$–$C_{10}$ alkyl, phenyl and substituted phenyl having up to two substituents which are independently selected from $C_1$–$C_4$ alkoxy, halo and $C_1$–$C_4$ alkyl and
$R_2$ is selected from trihalomethyl,

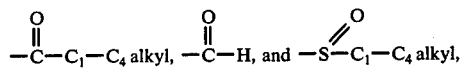

and pharmaceutically acceptable salts thereof.

$C_1$–$C_4$ alkyl includes linear and branched hydrocarbon alkyl such as methyl, sec. butyl, ethyl, —C(CH$_3$)$_3$ and the like. The L group includes $C_1$–$C_{10}$, linear and branched, hydrocarbon alkyl such as methyl, n-decyl, tert. butyl, isoamyl, n-heptyl and the like with $C_1$–$C_4$ alkyl being preferred, and mono- and di- substituted phenyl such as 4-tert. butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with mono- substituted phenyl preferred. The trihalomethyl substituent includes the trichloro, triiodo, trifluoro and tribromo moieties, with the trifluoromethyl group being preferred. R is isopropyl, sec. butyl or tert. butyl with tert. butyl being preferred.

The relative positions of the $R_2$ and —O—CH$_2$—CH(OR$_1$)—CH$_2$—NHR substituents in the formula I pyridine may be varied and all these variations are included. Thus the —O—CH$_2$—CH(OR$_1$)—CH$_2$—NHR group may be in the 3, 4 or 2 position in the pyridine ring while the $R_2$ may be in any other open position. Examples of these various isomers are 4-(—O—CH$_2$—CH(OH)—CH$_2$—NH isopropyl)-3-pentanoylpyridine, 4-(—O—CH$_2$—CH(OH)—CH$_2$—NH sec. butyl)-2-butylsulfinyl pyridine, 4-(O—CH$_2$—CH(OR$_1$)—CH$_2$—NH tert. butyl)-2-trichloromethyl pyridine, 3-(—O—CH$_2$—CH(OH)—CH$_2$—NHR)-4-formylpyridine, 3-(—O—CH$_2$—CH(OR$_1$)—CH$_2$—NHR)-5-tribromomethylpyridine, 3-(O—CH$_2$—CH(OH)—CH$_2$—NHR)-6-butyrylpyridine, 2-(O—CH$_2$—(CH(OH)—CH$_2$—NHR)-5-isopropylsulfinylpyridine, and the like.

Preferred compounds are those having the formula

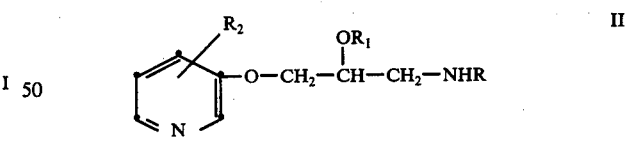

II with those Formula II compounds where $R_2$ is in the 2 position being especially preferred.

Another class of preferred compounds are those where —O—CH$_2$—CH(OR$_1$)—CH—NHR is in the two position. These compounds have the formula

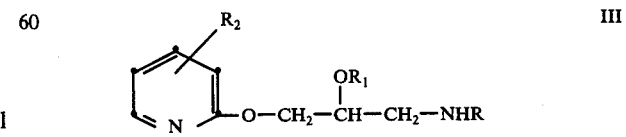

III

The compounds of formula III where $R_2$ is in the 3, 4 or 6 positions are more preferred and where $R_2$ is in the 3 or 4 position, the compounds are especially preferred.

The most preferred compounds of Formula III are those wherein $R_2$ is in the 3 position as illustrated by the following formula

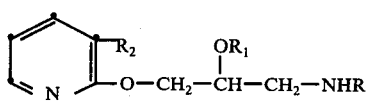

Examples of the most preferred compounds of formula IV are 2-(3-sec. butylamino-2-hydroxypropoxy)-3-trimethylacetylpyridine,
3-(3-isopropylamino-2-hydroxypropoxy)-3-butyrylpyridine,
2-(3-tert. butylamino-2-hydroxypropoxy)-3-n-butylsulfinylpyridine,
2-(3-isopropylamino-2-benzoyloxypropoxy)-3-triodomethylpyridine,
2-[3-sec. butylamino-2-(p-chlorobenzoyloxy)propoxy]-3-formylpyridine,
2-(3-tert. butylamino-2-hydroxypropoxy)-3-propionylpyridine,
2-(3-isopropylamino-2-undecanoyloxypropoxy)-3-ethylsulfinylpyridine,
2-[3-tert. butylamino-2-(p-methoxybenzoyloxy)propoxy]-3-acetylpyridine,
2-[3-sec. butylamino-2-(m-chlorobenzoyloxy)propoxy]-3-n-butysulfinylpyridine,
2-[3-isopropylamino-2-(2-bromo-4-methylbenzoyloxy)-propoxy]-3-pentanoylpyridine,
2-[3-tert. butylamino-2-(3,5-dimethoxybenzoyloxy)-propoxy]-3-trifluormethylpyridine,
2-(3-tert. butylamino-2-hydroxypropoxy)-3-sec. butylsulfinylpyridine,
2-(3-isopropylamino-2-octanoyloxypropoxy)3-acetylpyridine,
2-(3-tert. butylamino-2-isovaleryloxypropoxy)-3-tribromomethylpyridine
and the like.

Preferred compounds of Formula I–IV are those wherein $R_1$ is hydrogen. More preferrred are Formula I–IV compounds where $R_1$ is hydrogen and R is tert. butyl. Especially preferred Formula I–V compounds are those where $R_2$ is selected from -$CF_3$,

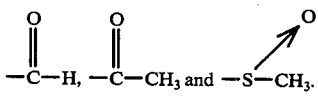

Most preferred compounds are the especially preferred compounds of Formula IV where $R_1$ is H and R is tert. butyl.

The substituted pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (*l*) and (*d*) or combinations of these symbols. The symbols (S) and (R) stand for sinister and rectus respectively and designate an absolute spatial configuration of the enantiomer.

The pyridines of the present invention can be prepared by any convenient process.

One such process involves the coupling of a halopyridine with a suitable substituted oxazolidine and hydrolysing the reaction product obtained. This process is illustrated by the following set of reaction equations:

Reaction A

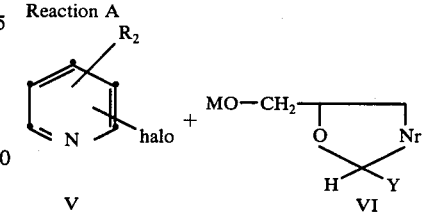

(1)

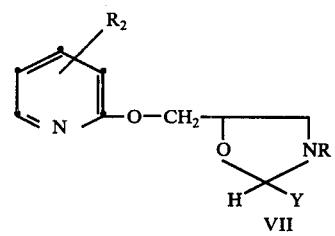

(2)

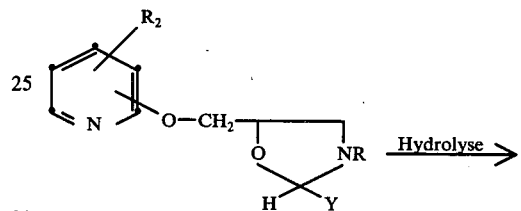

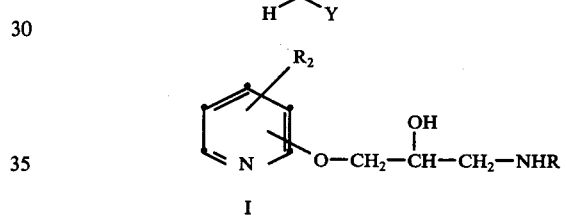

Halo may be Cl, Br and I, with Cl being preferred. M is an alkali metal, either potassium or sodium. Y can be hydrogen or the residue of any suitable aldehyde

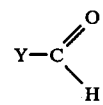

e.g. an arylaldehyde, such as benzaldehyde, naphthaldehyde and the like, or an alkanal such as acetaldehyde, butyraldehyde and the like. The process for preparing oxazolidines where M is hydrogen is disclosed in U.S. Pat. No. 3,718,647 and U.S. Pat. No. 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula VI) by reacting the oxazolidine

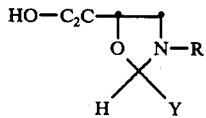

VIII with the Formula V pyridine in the presence of a strong base such as an alkali metal alkoxide (e.g. K—O—C—(CH$_3$)$_3$) or sodium hydride.

The coupling reaction can be carried out at temperatures ranging from about 0° to about 100° C. A temperature range of about 10° to about 50° C is preferred. The reaction is generally carried out in a solvent. Any suitable solvent may be used. Examples of useful solvents are dimethylformamide, dimethylsulfoxide, hexamethylphosphoramide, tert. butanol, alkanols and the like. The hydrolysis is carried out using conventional acid hydrolysis reagent and techniques e.g. treatment with a solution of any strong mineral acid such as HCl or H$_2$SO$_4$. The hydrolysis product can be directly obtained as the salt of the acid used for the hydrolysis. Ordinarily, the product I is recovered as the free base after conventional neutralization of the salt.

The coupling reaction is ordinarily carried out at atmospheric pressure. Higher pressures may be used if desired.

When a racemic oxazolidine (Formula VI or VIII) is used as a reactant, the product is obtained as a racemate. The racemate may be separated into its individual enantiomers by conventional resolution techniques.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Pyridines of the present invention wherein R$_1$ is other than hydrogen are conveniently prepared by treating the corresponding pyridine where R$_1$ is hydrogen with an appropriate acylating agent such as an acyl halide, e.g. undecanoyl chloride, pivaloyl chloride, benzoylchloride, p-methoxybenzoyl chloride, an anhydride e.g. acetic anhydride, and the like. The reaction is illustrated by the following equations:

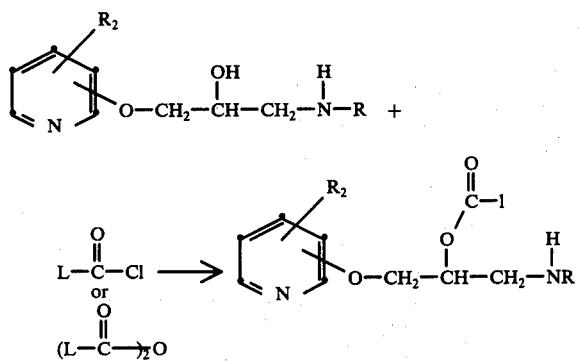

The compounds of the present invention also include the pharmaceutically acceptable salts of the novel pyridines. These salts are generally salts of the Formula I and II pyridines and organic or inorganic acids. These salts are prepared by treating the pyridine with an appropriate amount of a useful acid, generally in a suitable solvent. Examples of useful organic acids are carboxylic acids such as maleic acid, acetic acid, tartaric acid, propionic acid, fumaric acid, isethionic acid, succinic acid, pamoic acid, oxalic acid, pivalic acid and the like; useful inorganic acids are hydrohalo acids such as HCl, HBr, HI; sulfuric acid, phosphoric acid and the like.

The hydrochloride and hydrogen maleate salts are examples of preferred salts.

The compounds of the present invention have antihypertensive activity of rapid onset and are also β-adrenergic blocking agents. This antihypertensive activity is believed to the the result of peripheral vasodilation via a mechanism not directly related to β-adrenergic blockade. One advantage the present pyridines have over ordinary β-adrenergic agents is that the antihypertensive effect is immediate and generally of extended duration.

This rapid onset antihypertensive activity is determined by administering (orally) a representative pyridine of the present invention to spontaneously hyertensive (SH) rats and measuring the effect on blood pressure. Examples of representative compounds having this antihypertensive activity are (S)-2-(3-tert. butylamino-2-hydroxypropoxy)-3-trifluormethylpyridine and (S)-2-(3-tert. butylamino-2-hydroxypropoxy)-3-formylpyridine.

The β-adrenergic blocking activity of the present pyridines is determined by measuring the ability of a representative pyridine to block isoproterenol induced β-adrenergic stimulant effects such as heart rate increase, hypotension and bronchodilation, in animals.

The ability of the present pyridines to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as antihypertensives and/or β-adrenergic blocking agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like — or dissolved, dispersed or emulsified in a suitable liquid carrier — or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form requires. Conventional procedures are used to prepare the pharmaceutical formulations.

The dosage level for the present compounds may be varied from about 0.01 mg. to about 50 mg, per kilogram of animal body weight per day. Daily doses ranging from about 0.04 to about 2.5 mg/kg are preferred, with about 0.08 to about 1.25 mg/kg being a more preferred range. Oral administration is preferred. Either single or multiple daily doses may be administered depending on unit dosage.

Thus, another embodiment of this invention is a pharmaceutical composition containing an antihypertensive and/or β-adrenergic blocking amount of a compound of the present invention.

The following examples illustrate the preparation of representative examples of the present pyridines. Where no isomer designation is indicated, the product is the racemate. All parts are by weight unless otherwise noted. The R$_2$ substituted -2-halopyridine intermediates used in the example can be prepared as described in the article by D. Bonnetaud et al. in Journal of Heterocyclic Chemistry 9, 165–166 (1972).

EXAMPLE 1

S-3-Formyl-2-(3-tert. butylamino-2-hydroxypropoxy)pyridine hydrogen maleate

Step A

A solution of 2-chloro-3-pyridinecarboxaldehyde (3.20 g, 23.3 mmol) and ethylene glycol (2 ml) in 30 ml benzene is refluxed under $N_2$ for 20 hours with removal of water. The benzene solution is washed with saturated aqueous $Na_2CO_3$, dried ($Na_2SO_4$), filtered, and concentrated in vacuo to a solid which is triturated with cold hexane and filtered to give 4.0 g of the ethylene acetal of said aldehyde, mp 55°–56° C.

Step B

A suspension of NaH (1.0 g of ca. 50% mineral oil emulsion) in 20 ml N,N-dimethylformamide is treated with 4.7g (20 mmol) S-2-phenyl-3-tert. butyl-5-hydroxymethyloxazolidine with stirring under nitrogen at room temperature until hydrogen evolution ceases (about 1 hour). The acetal prepared in Step A is added and the mixture heated 1 hour at 80° C., cooled, quenched on ice, and extracted with ether. The ether extracts are washed with water and then extracted with two, 20 ml portions of 1.2N aqueous HCl and 20 ml water. The combined aqueous acid extracts are heated on the steam bath 30 minutes and stirred at room temperature overnight. The mixture is extracted with two volumes benzene, basified with solid $Na_2CO_3$ to pH 10 and extracted with ethyl acetate. The ethyl acetate extracts are washed with 50/50 mixture of $H_2O$/saturated aqueous $Na_2CO_3$, dried ($Na_2SO_4$), filtered and concentrated in vacuo yielding S-3-formyl-2-(3-tert. butylamino-2-hydroxypropoxy)pyridine product as an oil. This product is crystallized from isopropanol containing maleic acid (0.4M), to obtain the hydrogen maleate salt melting at 170°–171° C.

EXAMPLE 2

S-3-Acetyl-2-(3-tert. butylamino-2-hydroxypropoxy)pyridine

3-Acetyl-2-chloropyridine is converted to the ethylene ketal according to the procedure of Example 1, Step A and the crude ketal is reacted with S-2-phenyl-3-tert. butylamino-2-hydroxymethyloxazolidine as in Example 1, Step B to give the S-3-acetyl-2-(3-tert. butylamino-2-hydroxypropoxy)pyridine, m.p. 116°–117°.5° C, from n-butylchloride.

EXAMPLE 3

S-3-Trifluoromethyl-2-(3-tert. butylamino-2-hydroxypropoxy)pyridine

A. 2-Chloro-3-pyridinecarboxylic acid (50 g, 0.316 moles) is heated with 254 g of sulfur tetrafluoride and 40 ml of hydrogen fluoride in a stainless steel bomb at 150° C for 16 hours. The bomb is cooled, carefully vented, and the contents poured on ice. The pH is adjusted to approximately 6 with 10N aqueous sodium hydroxide and the product extracted with chloroform. The chloroform is dried over anhydrous sodium sulfate, filtered, and concentrated by fractional distillation. Distillation at atmospheric pressure gave a mixture of 2-chloro and 2-fluoro-3-trifluoromethylpyridines, b.p. 134°–317° C, which is used in the next step.

b. A suspension of soidum hydride (1 g, 50% emulsion in mineral oil) in 20 ml dry N,N-dimethylformamide is treated with S-2-phenyl-3-phenyl-3-tert. butyl-5-hydroxymethyloxazolidine (4.71 g, 20 mmol) and the mixture stirred 1 hr. under nitrogen until hydrogen evolution ceased. A 3.63 g sample of the product from step A is added, the mixture stirred one hour without external cooling, and then quenched on ice and extracted with ether. The ether extracts are extracted with two 20 ml portions of 1.2 N aqueous hydrochloric acid and water (20 ml).

The combined aqueous hydrochloric acid extracts are heated on the steam bath for 30 min., cooled, extracted with two volumes of ether, basified with solid sodium carbonate, and extracted with ethyl acetate. The ethyl acetate extracts are washed with saturated aqueous sodium carbonate, dried over anhydrous sodium carbonate, filtered, and concentrated in vacuo to give S-3-trifluoromethyl-2-(3-tert. butylamino-2-hydroxypropoxy)pyridine, m.p. 112°–113.5° C, after recrystallization from hexane-chloroform.

EXAMPLE 4

A. 2-Chloro-3-methylthiopyridine

To a solution of 3-amino-2-chloropyridine (12.2g, 0.095 mol), 48–50% fluoroboric acid (40 ml) and 95% EtOH (75 ml) was added at 0°–4° with stirring a solution of $NaNO_2$ (6.9, .1 mol) in $H_2O$ (20 ml). After complete addition, the solution was allowed to stir for 5 min. and then diluted with ether (150 ml.) The fluoroborate salt (21.7 g) was filtered and washed with ether (2×100 ml).

To a suspension of the fluoroborate salt (21.7g) in acetonitrile (20 ml) cooled in an ice bath was added a suspension of $NaSCH_3$ (7g, .1 mol) in acetonitrile (200 ml). After complete addition, the ice bath was removed and the solution allowed to stir at room temperature overnight. The suspension was concentrated to dryness and the residue was triturated with $CHCl_3$ (100 ml), filtered and concentrated to dryness. Distillation of the residual oil at 0.2 mm at 105°–108° C gave 2-chloro-3-methylthiopyridine (2.2g, 23%).

B. 2-(3-tert. Butylamino-2-hydroxypropoxy)-3-methylthiopyridine . Hydrogen Maleate Into a dried flask under nitrogen was placed S 2-phenyl-3-tert. butylamino-5-hydroxymethyloxazolidine (4.7g, 0.02 mol), 50% NaH (1g, .022 mol) and DMF (30 ml). The mixture was heated at 80° with stirring for 15 minutes cooled to room temperature and treated with a solution of 2-chloro-3-methylthiopyridine (2.0g, .015 mol) in DMF (5 ml). The mixture was allowed to stir at room temperature overnight and then poured into water (100 ml). The solution was extracted with ether (3×100 ml). The organic layers were backwashed with $H_2O$ (2×100 ml) and then with 3N HCl (3×75 ml). The acid extract was heated on a steam bath for 15 min., cooled and extracted with ether (2×100 ml). The aqueous layer was poured into saturated $Na_2CO_3$ (150 ml) and extracted with $CHCl_3$ (3×100 ml). The organic layer was dried over $Na_2SO_4$, filtered and concentrated to dryness. The residue was dissolved in ether and added to a solution of maleic acid in isopropyl alcohol (IPA). The precipitate was filtered off and recrystallized from ether-IPA to give 2-(3-tert. butylamino-2-hydroxypropoxy)-3-methylthiopyridine hydrogen maleate of m.p. 148°–149° C. (2.2 g, 32%).

C. 2-(3-tert. Butylamino-2-hydroxypropoxy)-3-methylsulfinylpyridine maleate salt To a solution of 2-(3-tert. butylamine-2-hydroxypropoxy)-3-methylthiopyridine (2.7g, 0.01 mol), MeOH (50 ml) and H$_2$O (50 ml) cooled to 0°–4° C was added dropwise a solution of NaIO$_4$ (3.0, 0.014 mol) in H$_2$O (100 ml). The mixture was allowed to warm to room temperature and stirred overnight. The suspension was then filtered and the solution was concentrated to half volume. The concentrated solution was extracted with CHCl$_3$ (4×100 ml). The organic layer was dried, filtered and concentrated to dryness. The residue was chromatographed on silica gel and the product eluted with 20% MeOH–CHCl$_3$. Crystallization on the maleic acid salt from diethyl ether/isopropanol gave 2-(3-tert. butylamino-2-hydroxypropoxy)-3-methylsulfinylpyridine hydrogen maleate of m.p. 98°–100° C (900 mg. 23%).

Isopropy or sec. butyl amino analogues of the compounds of the above examples are prepared by substituting suitable oxazolidines e.g. 3-phenyl-3-isopropyl-5-hydroxymethyloxazolidine, S-3-methyl-3-isopropyl-5-hydroxymethyloxazolidine, 3-sec. butyl-5-hydroxymethyloxazolidine for the S-2-phenyl-3-tert. butyl-5-hydroxymethyloxazolidine reactant.

Similarly, the derivatives of the Examples compounds where the 2-hydroxy group is acylated are prepared by treatment of the Example compound with a suitable reagent such as any acyl halide or anhydride to produce the corresponding ester derivative. For example, S-3-formyl-2-(3-tert. butylamino-2-hydroxypropoxy)pyridine is treated with trimethylacetylchloride in a suitable solvent to obtain the corresponding S-3-formyl-2-(3-tert. butylamino-2-pivaloyloxypropoxy)pyridine.

The present invention also includes the quaternary ammonium salts having the formula:

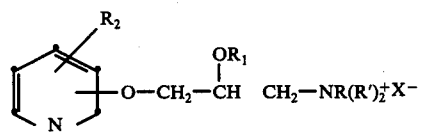

IX wherein R, R$_1$ and R$_2$ is defined above, R' is an alkyl (e.g. C$_1$–C$_4$ alkyl) or aryl (e.g. benzyl) group and X is a halogen especially Cl, Br or I. These quaternary salts are prepared using any convenient method. For example, they can be prepared by treating the compound of formula I with an alkyl or aryl halide such as methyliodide or benzylchloride to obtain the corresponding quaternary salt of formula IX.

The N-pyridine oxides have the formula

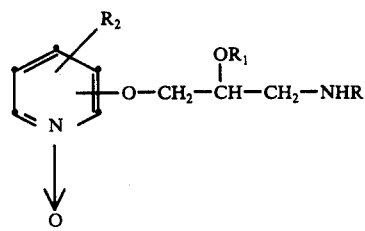

X with R, R$_1$ and R$_2$ as defined above, and include the acid addition salts and quaternary ammonium slats thereof. These N-oxides are also prepared using conventional reagents and procedure. For example, a convenient method of preparing these oxides is to treat the intermediate of Formula V with an oxidizing agent e.g. H$_2$O$_2$ using conventional reaction conditions to produce the oxidized intermediate having the formula

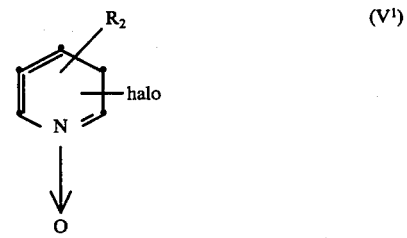

(V$^1$)

The formula V$^1$ compound is then substituted for the formula V compound in Reaction A above to obtain the N-pyridine oxide of Formula X.

Claims to the invention follow.

What is claimed is:

1. Compound having the formula

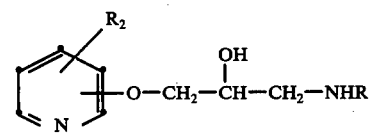

wherein
R is C$_3$–C$_4$ branched alkyl and
R$_2$ is selected from trihalomethyl, $$-\overset{O}{\underset{\|}{C}}-C_1-C_4\text{ alkyl}, \quad -\overset{O}{\underset{\|}{C}}-H \quad \text{and} \quad S-\overset{O}{\overset{\uparrow}{}}-C_1-C_4\text{ alkyl and}$$

pharmaceutically acceptable salt thereof.

2. Compound of claim 1 wherein R is tert. butyl.
3. Compound of claim 1 having the formula

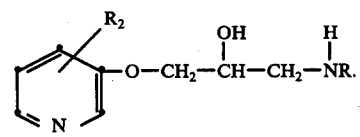

4. Compound of claim 3 wherein R$_2$ is in the 2-position.
5. Compound of claim 3 wherein R is tert. butyl.
6. Compound of claim 1 having the formula

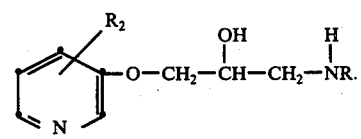

7. Compound of claim 6 wherein R is tert. butyl.
8. Compound of claim 6 wherein R$_2$ is in the 3, 4 or 6 position.
9. Compound of claim 6 wherein R$_2$ is in the 3 or 4 position.
10. Compound of claim 6 having the formula

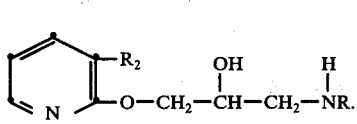

11. The compound of claim 10 wherein R is tert. butyl.

12. The compound of claim 10 wherein $R_2$ is selected from $-CF_3$,

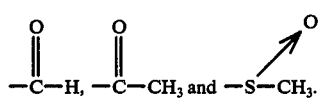

13. The compound of claim 12 wherein $R_1$ is hydrogen and R is tert. butyl.

14. The compound of claim 13 wherein $R_2$ is $-CF_3$.

15. The compound of claim 13 wherein $R_2$ is

16. The compound of claim 13 wherein $R_2$ is

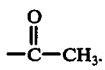

17. The compound of claim 13 wherein $R_2$ is

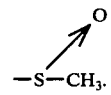

18. The compound of claim 1 having the S-isomer configuration.

19. The compound of claim 1 having the R-isomer configuration.

20. Compound having the formula

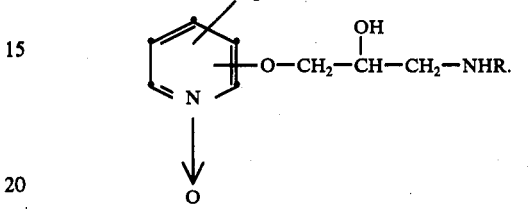

wherein R and $R_2$ are defined as in claim 1 and pharmaceutically acceptable salt thereof.

21. A method of treating hypertension in hypertensive humans which comprises oral, inhalation, suppository or parenteral administration of an effective amount of a compound of claim 1.

22. A pharmaceutical composition for treating hypertension comprising a therapeutically effective amount of a compound of claim 1 and pharmaceutically suitable compounding ingredient.

23. The compound of claim 14 having the S-isomer configuration.

24. The compound of claim 15 having the S-isomer configuration.

25. The compound of claim 16 having the S-isomer configuration.

26. The compound of claim 17 having the S-isomer configuration.

* * * * *